United States Patent [19]

Cook et al.

[11] 4,436,092
[45] Mar. 13, 1984

[54] EXERCISE RESPONSIVE CARDIAC PACEMAKER

[75] Inventors: William A. Cook, Bloomington; Neal E. Fearnot; Leslie A. Geddes, both of West Lafayette, all of Ind.

[73] Assignee: Purdue Research Foundation, West Lafayette, Ind.

[21] Appl. No.: 379,667

[22] Filed: May 19, 1982

[51] Int. Cl.$^3$ ............................................... A61N 1/36
[52] U.S. Cl. ............................................. 128/419 PG
[58] Field of Search ...................... 128/419 PG, 419 P

[56] References Cited

U.S. PATENT DOCUMENTS

| | | | |
|---|---|---|---|
| 3,593,718 | 7/1971 | Krasner et al. | 128/419 P |
| 3,656,487 | 4/1972 | Gobeli | 128/419 P |
| 3,828,371 | 8/1974 | Purdy | 3/1 |
| 3,867,950 | 2/1975 | Fischell | 128/419 P |
| 3,877,438 | 4/1975 | Cannon | 128/419 PG |
| 3,921,642 | 11/1975 | Preston et al. | 128/419 PG |
| 4,181,133 | 1/1980 | Kolenik et al. | 128/419 PG |
| 4,201,219 | 5/1980 | Bozal Gonzalez | 128/419 PG |
| 4,202,339 | 5/1980 | Wirtzfeld et al. | 128/419 PG |
| 4,228,803 | 10/1980 | Rickards | 128/419 PG |
| 4,305,396 | 12/1981 | Wittkampf et al. | 128/419 PG |
| 4,313,442 | 2/1982 | Knudson et al. | 128/419 PG |
| 4,363,325 | 12/1982 | Roline et al. | 128/419 PG |
| 4,399,820 | 10/1983 | Wirtzfeld et al. | 128/419 PG |

OTHER PUBLICATIONS

"Non-Electrographic Indices of Optimal Pacemaker Rate", Griffin et al., *34th ACEMB*, Sep. 21–23, 1981, p. 202.

"A Physiologically Controlled Cardiac Pacemaker", Krasner et al., *JAMA*, Nov.–Dec. 1966, pp. 14–16, 22.

*Primary Examiner*—William E. Kamm
*Assistant Examiner*—Mitchell J. Shein
*Attorney, Agent, or Firm*—Woodard, Weikart, Emhardt & Naughton

[57] ABSTRACT

An exercise-responsive cardiac pacemaker is provided which physiologically controls the stimulation rate of a heart by sensing the venous blood temperature in the right ventricle of the heart. A temperature sensing means which includes a thermistor produces an output signal which is sent to an algorithm implementing means for implementing the output signal by an algorithm which represents the mathematical function between venous blood temperature in the right ventricle and heart rate in a normally functioning heart. The algorithm implementing means produces an output signal which is variable between a maximum and minimum level corresponding to the desired maximum and minimum levels of heart rate in a normally functioning heart. The algorithm implementing means is also programmable by telemetry after implantation. A cardiac pacemaker is connected to the algorithm implementing means and is responsive thereto in order to variably control the stimulation rate of the heart.

9 Claims, 4 Drawing Figures

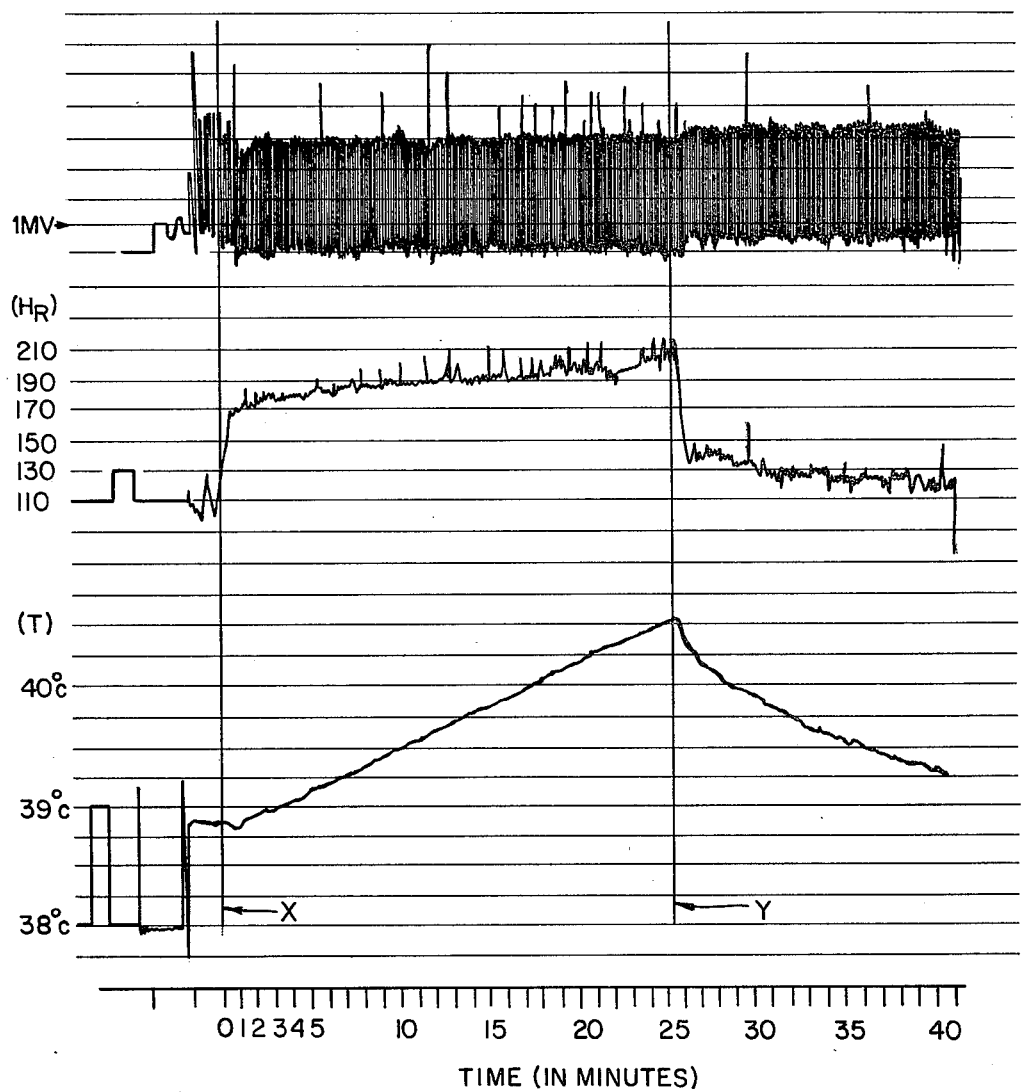
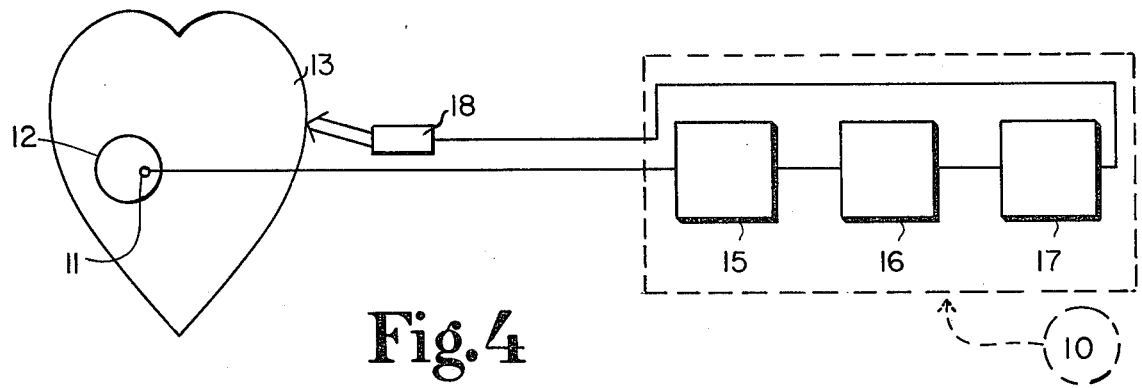

EXERCISE RESPONSIVE CARDIAC PACEMAKER

BACK OF THE INVENTION

1. Field of the Invention

The present invention relates to a cardiac pacemaker device and method for physiologically controlling the stimulation rate of a heart within a body.

2. Description of the Prior Art

The human body is equipped to adapt to the increased need for cardiac output during exercise. If the heart is functioning properly, the nervous system increases the heart rate and reduces peripheral resistance in response to exercise. Typical cardiac pacemakers stimulate the heart at a fixed rate, and therefore cannot change in order to meet the increased need for cardiac output during exercise. Thus, a person using a typical cardiac pacemaker is somewhat constrained in his daily activities.

The typical fixed-rate cardiac pacemaker produces electrical stimuli at a rate of approximately 72 beats per minute. The stimuli are applied to the heart through an electrode system in contact with the heart wall. Each time the electrical stimulus is delivered by the pacemaker and applied to the heart wall, a contraction of the myocardium results. The contraction pumps blood to the body.

From the orginal fixed-rate cardiac pacemaker evolved the demand pacemaker. The demand pacemaker ceases to produce a stimulus when a spontaneous heart beat is detected. The presence of a spontaneous heart beat is indicated by a normal QRS complex in the electro-cardiogram. Patients with intermittent conduction in the heart benefit from the demand pacemaker because this pacemaker does not compete with normal beats of the heart when and if they occur. Several modifications to the basic demand pacemaker have been made which attempt to better approximate a body's normal response. One such modified pacemaker allows the choice of two stimulation rates. Stimuli are produced at a nominal rate when the pacemaker is acting in the fixed-rate mode and at a lower rate when intermittent spontaneous heart beats are detected, thus allowing more time for the heart to beat spontaneously.

In addition to sensing the presence of electrical activity in the ventricle, sensing of atrial activity has also been used. A person may have normal atrial rhythm and some form of atrial-ventricular block. Such a person would benefit from an atrial-sensing pacemaker that delivers a stimulus to the ventricles after each atrial excitation. The atrial pacemaker has seen limited use because ventricular conduction problems often precipitate atrial tachycardia or fibrillation rendering the atrial-sensed pacemaker inactive.

In an effort to increase the efficiency of cardiac pacing, certain pacemakers use sensing of the electrogram in the atria and in the ventricles to allow atrial-ventricular synchrony to be restored. To produce each heart beat first the atria are stimulated. After a delay, nominally equal to the normal A-V node delay, the ventricles are stimulated. The addition of the atrial contraction produces the normal added filling of the ventricle that comes with synchronous atrial systole. Such a pacemaker, called the A-V sequential pacemaker, increases the end diastolic volume and therefore, the stroke volume, causing additional blood flow. In addition, A-V pacemakers incorporate dual sensing so that if the atria or ventricles beat, the spontaneously contracting chamber is not stimulated. More recently, a pacemaker with the combination of atrial and ventricular sensing, atrial and ventricular pacing, and atrial and ventricular inhibit has been developed. This pacemaker is commonly called a "DDD" pacemaker.

Pacemakers using each of the above modes may also be programmed after implantation. Each patient has slightly different requirements to optimally stimulate the heart. Therefore, if certain parameters of the pacemaker can be changed after implant, the pacemaker may be "individualized" to the patient's needs. Parameters that are programmable after implantation may include the rate, stimulus voltage, stimulus current, and electrogram sensitivity. In the case of the A-V sequential pacemaker, there is sensing and stimuli for both the atria and the ventricles that may be programmable in addition to the A-V delay time.

Since the first fixed-rate pacemaker, there have been many advances, but even with programmability the pacemaker does not adequately and reliably sense the body's need for more blood flow during exercise. Physiological pacemakers based on the electrical activity of the heart have not been applicable to a major portion of the pacemaker-using population. A patient with a partially denervated heart requires sensing of body cardiac output needs from a source other than electrical activity within the heart. There are many physiological indicators available from which the need for increased cardiac output may be sensed. In an attempt to provide sensing information, the nerves leading to the heart, in particular the sympathetic nerves, will provide information processed by the brain that naturally increases the heart rate. Unfortunately, current technology prohibits the use of a long term nerve impulse transducer.

The pH of the blood also has been measured and used to control the rate of a cardiac pacemaker. PH transducers that are implantable for long periods of time are however difficult to produce and therefore are not yet in common use.

The following list of references disclose devices which may have some general relevance to the present invention:

| Reference | Inventor |
|---|---|
| U.S. Pat. No. 3,867,950 | Fischell |
| U.S. Pat. No. 3,656,487 | Gobeli |
| U.S. Pat. No. 3,593,718 | Krasner |
| U.S. Pat. No. 3,828,371 | Purdy |
| U.S. Pat. No. 4,181,133 | Kolenik et al. |
| U.S. Pat. No. 4,023,121 | Alley, III |
| U.S. Pat. No. 4,228,8031 | Rickards |
| U.S. Pat. No. 4,201,219 | Bozal Gonzalez |
| U.S. Pat. No. 4,202,339 | Wirtzfeld et al. |

Journal of Association for Advancement of Medical Instrumentation, "A Physiologically Controlled Cardiac Pacemaker", Krasner; Voukydis; and Nardella, Nov.-Dec. 1966, Pages 14-16, and 20.

U.S. Pat. No. 3,867,950 to Fischel discloses a fixed rate rechargeable cardiac pacemaker which utilizes as its power source a single rechargeable cell battery which is recharged through the patient's skin by magnetic induction. The electronic pulse generating circuitry is designed such that the output pulse rate varies as a function of the battery voltage and also as a function of the body temperature. This device is different from the present invention in that the heart stimulation rate is controlled by ambient body temperature, in other words, a body core temperature which represents the average body temperature. Thus, ambient body temperature is measured by a charging capacitor having a high temperature coefficient located within the pulse generator circuitry. Since ambient body temperature does not vary appropriately as a function of muscle exertion, this device will not respond to a body's need for increased cardiac output due to muscular exertion.

U.S. Pat. No. 3,656,487 to Gobeli discloses an electronic demand heart pacemaker with different pacing and standby rates. The device stimulates heart rate at a first frequency in the continued absence of natural heart beats but allows the heart to beat naturally at any rate above a second lower standby frequency. The device reverts to a third frequency in a non-demand type operation in the presence of an interfering electrical noise pattern.

U.S. Pat. No. 3,593,718 to Krasner discloses a physiolgically controlled cardiac pacer which uses respiratory rate to vary the production of electronic pulses which aer fed to a constant current source connected to the ventricle. In another variation, pulses are fed to two separate constant current sources, one connected to the atrium and the other, with delay, to the ventricle.

U.S. Pat. No. 3,828,371 to Purdy discloses a self-contained artificial heart which is adapted to vary the pulse rate and the stroke length in response to blood pressure. Variations in blood pressure are detected by means of a pressure sensitive transistor, thereby varying the rate of pumping of blood in response to blood pressure.

U.S. Pat. No. 4,181,133 to Kolenik et al. discloses a programmable tachycardia pacer which performs the dual functions of demand pacing as well as standby tachycardia break up. A command parameter control is used for programmably controlling the parameters of the pacer operation as well as of the tachycardia recognition and response.

U.S. Pat. No. 4,023,121 to Alley discloses an oscillator for a demand heart pacer which produces stimulation pulses in an inhibit mode at a first frequency and stimulation pulses at a second fixed rate mode at a second frequency. The device additionally employs an oscillator inhibitor which operates to define a variable second half of a refractory period to distinguish noise at a frequency approximately twice that of an acceptable heart frequency.

U.S. Pat. No. 4,228,803 to Rickards discloses a physiologcially adaptive cardiac pacemaker having a demand generator which is sensitive to the electrical activity of the heart. The interval between a pacing stimulus delivered by a pacemaker generator and the evoked ventricular repolarization sets the escape interval of the generator for the subsequent stimulus, and thus physiologically controls the heart rate.

U.S. Pat. No. 4,201,219 to Bozal Gonzalez discloses a cardiac-pacemaker in which the generation of stimulation pulses is controlled by regulation signals detected in the nerves via receivers.

U.S. Pat. No. 4,202,339 to Wirtzfeld et al. discloses a cardiac pacemaker which measures the oxygen saturation of the blood as a control variable for influencing the frequency of stimulation. Determination of the blood oxygen saturation is made via light conductor probes implanted in the heart.

The publication entitled "A Physiologically Controlled Cardiac Pacemaker" by Krasner et al. discloses a cardiac pacemaker similar to that disclosed in U.S. Pat. No. 3,593,718 to Krasner, which uses respiratory rate to vary the production of electronic pulses to the heart.

One physiological indicator which responds directly to the need for higher cardiac output due to exercise, but which is not disclosed in any of the above references, is venous blood temperature. When a person exercises, the muscles do work. Since the muscles are not completely efficient, they also produce heat. It is the task of the blood stream to dispose of the additional heat produced by the exercising muscles.

The heat produced by a muscle raises the temperature of the blood leaving it. This blood returns directly to the right heart before passing through heat dissipating tissue. The blood returning to the right heart therefore contains information about the work output of the body musculature. Right ventricular blood is a combination of blood from the upper body via the superior vena cava and from the lower body via the inferior vena cava. The blood from these two areas of the body is mixed in the right atrium and again in the right ventricle where it is joined with blood drained from the heart. Thus, right ventricular blood temperature is the average temperature returning from all the body and so reflects the average work output of the body. Since the heat causing the temperature rise during exercise is generated by exercising muscles, the right ventricular blood temperature reflects the average level of exercise and hence, the need for increased cardiac output or increased heart rate.

Accordingly, it is an object of the present invention to provide an improved cardiac pacemaker in which stimulation of the heart is varied in accordance with the level of muscular exertion.

This and other objects and advantages of the present invention will become more apparent in the following figures and detailed description.

SUMMARY OF THE INVENTION

One embodiment of the present invention includes a temperature sensing means for sensing a non-ambient body temperature which is related by an algorithm to heart rate in a normally functioning heart. The temperature sensing means is inserted into a desired location within a body wherein the temperature at said location is a non-ambient body temperature which is related to heart rate in a normally functioning heart by said algorithm. The temperature sensing means produces an output signal which is received by an algorithm implementing means connected to the temperature sensing means. The algorithm implementing means implements the output signal by an algorithm which represents the mathematical function between the non-ambient body temperature and heart rat in a normally functioning heart. A cardiac pacemaker is connected to the algorithm implementing means and is responsive thereto in order to variably control the stimulation rate of the heart.

BRIEF DESCRIPTION OF THE DRAWINGS

FIG. 1 is a graph of the electrogram of a body during periods of muscular exertion and rest.

FIG. 2 is a graph showing the relationship of right ventricular venous blood temperature with respect to time during periods of muscular exertion and rest.

FIG. 3 is a graph showing the relationship of heart rate with respect to time during periods of muscular exertion and rest.

FIG. 4 is a schematic illustration of the present invention in block diagram.

DESCRIPTION OF THE PREFERRED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

It has been determined that there exists a relationship between a body's need for increased cardiac output due to exercise and venous blood temperature. Further, because blood entering the right ventricle of the heart is combination of blood from the upper body via the superior vena cava and from the lower body via the inferior vena cava, the right ventricle is an appropriate location from which to determine the average temperature of blood returning from all of the body's musculature. It is important to note that this temperature will differ from body core temperature and therefore represents a non-ambient body temperature. FIGS. 1, 2, and 3 are typical graphs of the electrogram, right ventricular blood temperature, and heart rate, respectively, versus time in a normal test dog. Point X indicates the moment in time exercise was begun while Point Y indicates the moment in time exercise was ceased. It is readily observed from FIG. 3 that the heart rate increased with respect to time during the period of exercise and decreased with respect to time during the subsequent period of rest. FIG. 2 shows that the right ventricular blood temperature also increased with respect to time during the period of exercise and decreased with respect to time during the subsequent period of rest. Based upon the observed relationship between the heart rate and venous blood temperature in the right ventricle, a simple, practical, and implementable algorithm may be derived to produce a physiologically optimal heart rate. Thus, the relationship between venous blood temperature in the right ventricle and heart rate may be described by the following equation:

$$H_R = A + B(T - T_0) + C \sin(dT/dt)$$

In the above equation, $H_R$ represents the instantaneous heart rate in beats per minute; A represents the resting heart rate in beats per minute; B represents the slope of the heart rate versus temperature curve during exercise; T represents the smoothed or filtered instantaneous right ventricular temperature in degrees Centigrade; $T_0$ is the resting right ventricular temperature in degrees Centigrade; C represents the initial rise in the heart rate in beats per minute at the beginning of exercise divided by the slope of the temperature versus time curve during exercise; and $dT/dt$ represents the derivative of temperature with respect to time.

It should be understood that other mathematical equations could be derived in order to approximate the observed relationship between venous blood temperature and heart rate, and thus may also be used as control algorithms. Further, the equation described above may be simplified while producing a slightly suboptimal response.

At this point it should also be noted that while the above equation was derived from experimental data on test dogs, this data generally agrees with data taken from human subjects and reported in the literature. The observed results are basically similar to the human data except that the slope of the temperature versus time curve in the human data suggests an exponential shaped increase in temperature versus time while the data on test dogs shows a near linear increase in temperature in many cases. This difference is probably because the human species perspires to dissipate excess heat while a dog dissipates heat by panting. Since perspiration is a much more efficient method for heat dissipation than panting, the heat dissipated by perspiration equals the excess heat produced by exercise at a lower temperature than by panting. Hence, the coefficients in the above equation and perhaps the form of the equation may be slightly different for human subjects.

Referring now to FIG. 4, the exercise-responsive pacemaker 10 of the present invention is shown in a schematic block diagram. Thermistor 11 is shown placed within the right ventricle 12 of the heart 13. Thermistor 11 is powered by pacemaker 10. Since the resistance across thermister 11 varies in a known manner with temperature, the output voltage wave across thermistor 11 is an analog representation of the instantaneous right ventricular blood temperature. Thermistor 11 is connected to algorithm implementing means 15 which implements the output voltage wave from thermistor 11 according to the above described equation. It is to be understood that A, B, C, and $T_0$ are constants which are determined by experimental data upon the particular subject for which the device of the present invention is to be used. For this reason, algorithm implementing means 15 may be programmed by using any conventional means such as programmable control chips. Programming algorithm implementing means 15 may be performed non-invasively by employing a parameter control circuit which is controlled externally by telemetric signals, such as is disclosed in U.S. Pat. No. 4,164,944 to Alley, et al. Other examples of programmable pacemakers are model numbers 325 and 325T programmable pacemakers produced by Cook Pacemaker Corporation of Leechburg, Pa.

Algorithm implementing means 15 is connected to pulse generator control circuit 16 which receives the output wave from the algorithm implementing means 15. Pulse generator control circuit 16 logically determines in a well known manner the pulse rate to be generated by pulse generating means 17 which is connected to pulse generator control circuit 16. It is to be understood that pulse generating means 17 may be of any suitable design and is capable of producing a stream of pulses at any desired number of discrete frequency levels. It should also be understood that pulse generating control circuit 16 controls the frequency of pulses generated by pulse generating means 17 so that the frequency of pulses will be within selected minimum and maximum levels corresponding to or within the maximum and minimum levels found in a normally functioning heart. Thus, pulse generating means 17 sends a stream of pulses to electrode means 18 which is attached to the heart wall in a conventionally known manner for electrical stimulation of the heart.

It should be obvious that pulse generating control circuit 16 and pulse generating means 17 may be designed to provide any of the several types of heart stimulation techniques currently in use. For instance, pulse generating control circuit 16 and pulse generating means 17 may be designed for a demand pacemaker function in which pulse generating means 17 pulses at a variable controlled rate when no intermittent spontaneous heart beat is detected and at a lower fixed rate when intermittent spontaneous heart beats are detected. Thus, more time is allowed for the heart to beat spontaneously if a spontaneous beat is detected. Alternatively, pulse generating control circuit 16 and pulse generating means 17 may also be designed to perform as an A-V sequential pacemaker. In this application, sensing of the electrogram in the atrium and the ventricle is performed by an electrode in each respective chamber. Stimulation of the atria and ventricles can be provided as required in order to restore atrial-ventricular synchrony and to provide increased blood flow with increased levels of exertion. One type of A-V sequential pacemaker is disclosed in U.S. Pat. No. 4,192,316 to Walters, et al.

In order to use the device of the present invention in order to variably control the stimulation rate of the heart in accordance with the level of muscular exertion of the body, thermistor 11 is inserted within the right ventricle 12 of heart 13 by suitable means, such as by mounting the thermistor upon the same lead upon which the electrode means 18 is mounted. Algorithm implementing means 15, pulse generator control circuit 16, and pulse generating means 17 may be contained within a common housing which is implanted subcutaneously. Alternatively, algorithm implementing means 15, pulse generator control circuit 16, and pulse generating means 17 may be a non-implantable unit which is located externally of the body to provide temporary artificial heart stimulation. In either case, stimulation of the heart is then provided by electrodes attached to the heart wall in a manner well known in the art. Thus, it is seen that the exercise responsive pacemaker of the present invention discloses a device which is highly suitable for providing stimulation of the heart at a rate which is physiolgocially controlled in order to provide increased cardiac output during periods of muscular exertion.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A cardiac pacemaker including means for variably controlling the stimulation rate of the heart according to the level of muscular exertion in the body, comprising:

a temperature sensing means for sensing a non-ambient body temperature, said non-ambient body temperature related by an algorithm to heart rate in a normally functioning heart, said temperature sensing means producing an output signal;

an algorithm implementing means connected to said temperature sensing means for implementing said output signal by an algorithm which represents the mathematical function between said non-ambient body temperature and heart rate in a normally functioning heart; and a cardiac pacemaker connected to said algorithm implementing means and responsive thereto in order to variably control the stimulation rate of said heart.

2. The cardiac pacemaker of claim 1, wherein said algorithm implementing means output signal is a variable between a maximum and minimum level corresponding to the desired maximum and minimum levels of heart rate in a normally functioning heart.

3. The cardiac pacemaker of claim 2, wherein said temperature sensing means senses blood temperature.

4. The cardiac pacemaker of claim 3, wherein said temperature sensing means senses venous blood temperature in the right ventricle of said heart.

5. The cardiac pacemaker of claim 4, wherein said algorithm implementing means is programmable by telemetry after said cardiac pacemaker is implanted in said body.

6. The cardiac pacemaker of claim 5, wherein said temperature sensing means includes a thermistor.

7. A method for variably controlling the stimulation rate of the heart according to the level of muscular exertion in a body, comprising the steps of:

(a) measuring the temperature at a desired location within said body at which location the temperature is a non-ambient body temperature which is related to heart rate in a normally functioning heart by an algorithm; and (b) controlling a cardiac pacemaker by said measured temperature so as to cause said cardiac pacemaker to provide electrical stimulation to a heart at a rate which is related by said algorithm to the temperature measured.

8. The method of claim 7, wherein step (a) includes inserting a temperature sensing means within the blood stream in order to sense blood temperature.

9. The method of claim 8, wherein step (a) includes inserting said temperature sensing means via a catheter within the right ventricle of said heart in order to sense venous blood temperature.

* * * * *

REEXAMINATION CERTIFICATE (1358th)
United States Patent [19]
Cook et al.

[11] B1 4,436,092
[45] Certificate Issued  Sep. 25, 1990

[54] EXERCISE RESPONSIVE CARDIAC PACEMAKER

[75] Inventors: William A. Cook, Bloomington; Neal E. Fearnot; Leslie A. Geddes, both of West Lafayette, all of Ind.

[73] Assignee: Purdue Research Foundation, Lafayette, Ind.

Reexamination Request:
No. 90/001,612, Oct. 3, 1988

Reexamination Certificate for:
Patent No.: 4,436,092
Issued: Mar. 13, 1984
Appl. No.: 379,667
Filed: May 19, 1982

[51] Int. Cl.$^5$ ............................................. A61N 1/365
[52] U.S. Cl. ............................................. 128/419 PG
[58] Field of Search ..................... 128/419 P, 419 PG

[56] References Cited

U.S. PATENT DOCUMENTS

| | | | |
|---|---|---|---|
| 4,164,944 | 8/1979 | Alley, III et al. | 128/419 PG |
| 4,201,219 | 5/1980 | Bozal Gonzalez | 128/419 PG |
| 4,365,633 | 12/1982 | Loughman et al. | 128/419 PG |
| 4,399,820 | 8/1983 | Wirtzfeld et al. | 128/419 PG |
| 4,428,378 | 1/1984 | Anderson et al. | 128/419 PT X |
| 4,719,920 | 1/1988 | Alt et al. | 128/736 X |

FOREIGN PATENT DOCUMENTS

| | | |
|---|---|---|
| 7606824 | 3/1976 | Fed. Rep. of Germany . |
| 2609365 | 9/1977 | Fed. Rep. of Germany . |

OTHER PUBLICATIONS

Csapo et al., "Autoregulation of Pacemaker Rate by Blood Temperature," VIII World Congress of Cardiology, Tokyo, Japan, Sep. 17-23, 1978.

*Primary Examiner*—Francis J. Jaworski

[57] ABSTRACT

An exercise-responsive cardiac pacemaker is provided which physiologically controls the stimulation rate of a heart by sensing the venous blood temperature in the right ventricle of the heart. A temperature sensing means which includes a thermistor produces an output signal which is sent to an algorithm implementing means for implementing the output signal by an algorithm which represents the mathematical function between venous blood temperature in the right ventricle and heart rate in a normally functioning heart. The algorithm implementing means produces an output signal which is variable between a maximum and minimum level corresponding to the desired maximum and minimum levels of heart rate in a normally functioning heart. The algorithm implementing means is also programmable by telemetry after implantation. A cardiac pacemaker is connected to the algorithm implementing means and is responsive thereto in order to variably control the stimulation rate of the heart.

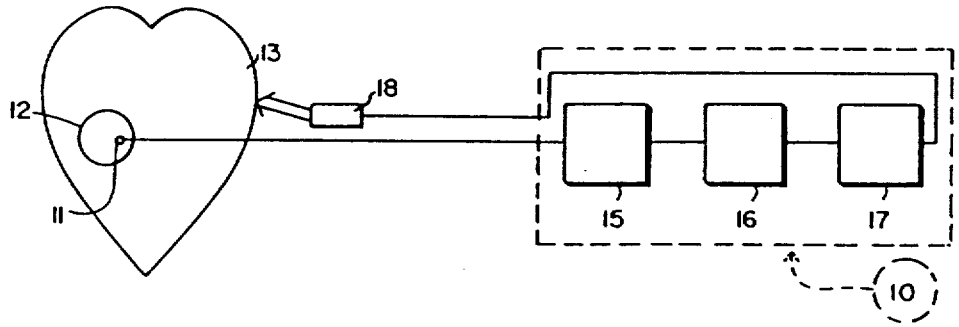

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 7 are determined to be patentable as amended.

Claims 2-6 and 8-9, dependent on an amended claim, are determined to be patentable.

1. A cardiac pacemaker [including means] for [variably] controlling the stimulation rate of the heart according to the level of muscular exertion in the body, comprising:
   a temperature sensing means for sensing a non-ambient body temperature, said non-ambient body temperature related by an algorithm to heart rate in a normally functioning heart, said temperature sensing means producing an output signal;
   an algorithm implementing means connected to said temperature sensing means for implementing said output signal by an algorithm which represents the mathematical function between said non-ambient body temperature and heart rate in a normally functioning heart; and
   [a cardiac pacemaker] *variable rate control means* connected to said algorithm implementing means and responsive thereto in order to variably control the stimulation rate of said heart.

7. A method for variably controlling the stimulation rate of the heart according to the level of muscular exertion in a body, comprising the steps of:
   (a) measuring the temperature at a desired location within said body at which location the temperature is a non-ambient body temperature which is related to heart rate in a normally functioning heart by an algorithm; [and]
   (b) *implementing said measured temperature by an algorithm which represents the mathematical function between said non-ambient body temperature and heart rate in a normally functioning heart;*
   [(b)] *(c) variably* controlling *the rate of* a cardiac pacemaker [by said measured temperature] so as to cause said cardiac pacemaker to provide electrical stimulation to a heart at a rate which is related by said *implemented* algorithm to the temperature measured.

* * * * *